United States Patent
Gill et al.

(10) Patent No.: US 7,622,030 B2
(45) Date of Patent: Nov. 24, 2009

(54) GENERAL AND LOCALIZED CORROSION RATE MEASUREMENTS

(75) Inventors: Raymond Paul Gill, Grange over Sands (GB); Vladimir Jovancicevic, Richmond, TX (US); Wai Yeung Mok, Manchester (GB); Paul Hammonds, Katy, TX (US)

(73) Assignee: Baker Hughes Incorporated, Houston, TX (US)

(*) Notice: Subject to any disclaimer, the term of this patent is extended or adjusted under 35 U.S.C. 154(b) by 644 days.

(21) Appl. No.: 11/499,630

(22) Filed: Aug. 4, 2006

(65) Prior Publication Data

US 2007/0017822 A1    Jan. 25, 2007

Related U.S. Application Data

(63) Continuation-in-part of application No. 11/262,861, filed on Oct. 31, 2005, which is a continuation-in-part of application No. 11/086,191, filed on Mar. 21, 2005, now Pat. No. 7,368,050.

(60) Provisional application No. 60/556,644, filed on Mar. 26, 2004.

(51) Int. Cl.
*G01N 17/04* (2006.01)
*G01R 27/08* (2006.01)
*G01N 27/00* (2006.01)

(52) U.S. Cl. ............... 205/775.5; 205/776.5; 324/700; 324/721; 324/71.2; 204/404

(58) Field of Classification Search .......... 204/404; 324/700, 721, 71.2; 205/776.5, 775.5
See application file for complete search history.

(56) References Cited

U.S. PATENT DOCUMENTS

| 5,139,627 A | 8/1992 | Eden et al. |
| 5,275,704 A * | 1/1994 | Yang ..................... 205/777 |
| 5,888,374 A | 3/1999 | Pope et al. |
| 6,280,603 B1 | 8/2001 | Jovancicevic et al. |
| 2005/0211570 A1 | 9/2005 | Jovancicevic et al. |

FOREIGN PATENT DOCUMENTS

| GB | 2 218 521 A | 11/1999 |
| GB | 2 365 977 A | 2/2002 |

OTHER PUBLICATIONS

B. H. Vassos, et al., Electroanalytical Chemistry, 1983, pp. 230-235, Wiley-Interscience, NY.
J. L. Dawson, et al., "Electrochemical Measurements for Inhibitor Assessments," Corrosion 93, NACE Annual Conference and Corrosion Show, Paper No. 108, 1993, pp. 108/1-108/19.

* cited by examiner

*Primary Examiner*—Alexa D Neckel
*Assistant Examiner*—Gurpreet Kaur
(74) *Attorney, Agent, or Firm*—Mossman Kumar & Tyler PC

(57) ABSTRACT

Simultaneous determination of general corrosion and localized corrosion rate measurements is achieved with polarization applied by the electrodes themselves rather than externally applied polarization. Two or more working electrodes may be galvanically coupled. A localized pitting corrosion event on one of the electrodes will lead to a potential transient. The area within the potential transient is measured with the baseline being the initial starting potential. This gives localized corrosion as a function of time. The relationship $R_p = \Delta V/\Delta I$ is calculated, where $R_p$ is the polarization resistance of the working electrodes and is a measure of generalized corrosion rate.

13 Claims, 4 Drawing Sheets

Natural Transient

GENERAL AND LOCALIZED CORROSION RATE MEASUREMENTS

CROSS-REFERENCES TO RELATED APPLICATIONS

This application is a Continuation-in-Part application of U.S. patent application Ser. No. 11/262,861 filed Oct. 31, 2005, which in turn is a Continuation-in-Part application of U.S. patent application Ser. No. 11/086,191 filed Mar. 21, 2005, which in turn claims the benefit of U.S. Provisional Patent Application No. 60/556,644 filed on Mar. 26, 2004, all of which are incorporated herein by Reference in their entirety.

BACKGROUND

1. Technical Field

The present invention relates to electrochemical methods and systems for calculating corrosion rate, particularly to methods and techniques for evaluating both generalized and localized corrosion, and most particularly relates in a non-limiting embodiment, to methods and techniques for simultaneously determining and calculating generalized corrosion and localized corrosion in hydrocarbon pipelines, transportation systems, processing vessels and fluid handling equipment.

2. Description of the Related Art

General corrosion rate measurements, such as Linear Polarization Resistance (LPR) measurements, typically involve some sort of external polarization, where the resultant current response is used to calculate the Resistance to Polarization, Rp. These methods do not readily give a measure of the localized corrosion.

Localized corrosion of equipment is a serious problem in many industries and processes. In particular, corrosion failures in many oil and gas production systems, oil/gas/water transmission pipelines, petrochemical and chemical processing plants, fossil fuel and nuclear power plants involve localized corrosion. Localized corrosion may result in loss of production, increase in maintenance cost, environmental pollution and potential health and safety hazards, etc. It is important that the occurrence of localized corrosion is identified and the severity determined in advance of structural failure, particularly catastrophic failure. In addition, the ability of chemical introduction and other techniques to inhibit and/or prevent localized corrosion needs to be determined.

Localized corrosion is the selective removal of metal by corrosion at small areas or zones on a metal surface in contact with a corrosive environment, usually a liquid. While pitting is a localized corrosion, the locally corrosive pits may eventually cover substantial portions of a corroded electrically conductive article's surface. Localized corrosion may occur when small local sites are attacked at a much higher rate than the rest of the surface. Alternatively, a film or surface may protect the majority of the structure, while a relatively small area is under localized corrosion attack. Localized corrosion occurs when corrosion works with other destructive forces such as stress, fatigue, erosion and chemical attacks. Localized corrosion can cause more damage than any of these destructive forces individually.

The problems resulting from localized corrosion have been dealt with for many years with variable success. Localized corrosion is highly stochastic in nature and its occurrence is fairly unpredictable. Currently, localized corrosion is studied or monitored by measuring directly relatively large features (e.g. pits) on the surface by using standard optical microscopy with limited spatial resolution. Indirect methods are also used, such as electrochemical noise, to provide indication of the probability of localized (e.g. localization index) corrosion.

Although the above techniques are widely employed, they (1) possess limitations in that they only provide information on uniform (general) corrosion conditions because they provide an average signal for the surface of the electrode being monitored; and (2) depending upon the environment, metallic material, and corrosion type, the assumption that the corrosion rate is inversely proportional to the measured charge transfer or polarization resistance is invalid because the corrosion is of a localized nature. These problems have been addressed by monitoring localized corrosion via the utilization of electrochemical potential noise analysis.

Electrochemical noise (ECN) may be defined as the spontaneous fluctuations of current and potential generated by corrosion reactions. Various methods have been used to determine corrosion rates, including LPR. In LPR a direct current (DC) signal is applied to a corroding cell consisting of two or three electrodes and the resulting DC polarization is monitored. Provided that the applied current is small and that the potential shift is less than 20 millivolts (mV), the response is linear in most cases and the measured resistance, commonly known as the Polarization Resistance, Rp, may be related inversely to the rate of the uniform corrosion attack. Other techniques include the application of electrochemical impedance spectroscopy (EIS) in which a sine wave current or potential is applied. In a similar manner to the linear polarization technique, the sine wave potential or current resulting from the applied current or potential is monitored. Alternatively, a pseudo random noise signal can be applied to a corroding cell, with the electrochemical impedance obtained by time or frequency domain transformations.

The ECN technique tries to correlate the two signals using a range of mathematical methods. Standard mathematical techniques however simply treat the data as noise and work on factors such as the standard deviation and the mean. General corrosion is obtained from the ratio of standard deviation of voltage and standard deviation of current ($Rn=\sigma_v/\sigma_I$), while localized corrosion is defined as a ratio of standard deviation of current and mean value of current ($LI=\sigma_I/rms_I$). Localized corrosion can produce significant individual events that are analyzed incorrectly if they are considered as noise.

Alternatively, by coupling current analysis with electrochemical potential noise analysis further information can be obtained. For example, two similar electrodes can be coupled together via a zero-resistance ammeter (ZRA) with the output of the ZRA passed to the input of the electrochemical noise analysis system. In this way, the fluctuation of the coupling current may be analyzed in essentially a similar manner as for the electrochemical potential noise analysis described previously.

Systems which employ two working electrodes fabricated with the same material and exposed to the same corrosion conditions as the metallic surface to be tested are known. Such systems further employ a device for measuring the coupling current between the working electrodes, a device for measuring electrochemical potential noise originating from the electrodes, and a device for comparing the coupling current with the electrochemical current noise to provide an output indicative of the degree to which corrosion is localized. The systems utilize open circuit potential conditions, employing two working electrodes in an electrolyte environment wherein both electrodes are short circuited with a low resistance amp meter. The current between these two working electrodes is the result of corrosion occurring on them, with the measurement of the net current relating to the corrosion on both of them. Disadvantages of this system, however, range from the fact that the working electrodes need to be identical to obtain accurate readings and obtaining such identical electrodes is difficult, if not impossible. Another problem is that it is unknown which electrode is responding to reveal the corrosion, due to the fact that this system requires the use of two working electrodes which limits where such systems can be employed. Furthermore, distinguishing between various types of localized corrosion is, at minimal, difficult due to the fact that both electrodes contribute to the system response.

Localized Corrosion Monitoring (LCM™) looks at the potential of an electrode with respect to time. Individual localized events tend to give a potential transient typically due to a pitting, or any other form of localized corrosion (e.g. crevice, SCC), event. The magnitude of the current involved in this pitting event can be calibrated with a periodic polarization using either a small LPR type polarization, or a larger scale polarization of the same magnitude as the pitting event. In this way a V/I conversion curve can be constructed for conversion of the potential transient into a current transient. The current can then be used to calculate charge and ultimately metal loss associated with the individual pitting event.

What is needed in the art is a simplified corrosion rate detection system and method by providing corrosion detection calculation capability for both generalized and localized metal corrosion, without the use of external polarization required for LPR and LCM techniques.

SUMMARY

In one non-limiting embodiment there is provided a method for measuring generalized corrosion and localized corrosion rates that involves (a) placing at least three electrodes in proximity to one another. At least two working electrodes are galvanically coupled via a zero- or low-resistance ammeter used to monitor the potential of the electrodes. There is present at least a reference electrode of a material resistant to localized attack which is used to monitor the potential of the galvanically coupled electrodes. The method further includes (b) detecting transients in potential data for a localized corrosion event and calculating an area within the transient having units of volts-time. Additionally the method includes (c) calculating the change in the magnitude of the current data passed during the potential transient for the same time period as (b) and giving it a value with units of current-time (coulombs). The method additionally concerns (d) dividing the volts-time by the current-time to give the polarization resistance (Rp) as a measure of general corrosion rate. Further, the method includes (e) doubling the charge in (c) to calculate the metal loss caused by the localized corrosion event.

In another non-limiting embodiment there is provided an apparatus for measuring generalized corrosion and localized corrosion rates that includes three electrodes in proximity to one another in a corrosive acid solution. The electrodes include two working electrodes galvanically coupled via a zero- or low-resistance ammeter, and a reference electrode of a material resistant to localized attack. The system further includes a mechanism for applying an occasional polarization to the working electrodes to determine the general corrosion rate by offsetting one of the electrodes against the other.

The method and apparatus or system of the present invention may be implemented as a set computer executable of instructions on a computer readable medium, including, but not necessarily limited to, ROM, RAM, CD-ROM, Flash RAM or any other computer readable medium, now known or unknown that when executed cause a computer to implement the functions of the present invention.

Examples of the more important features thus have been summarized rather broadly in order that the detailed description thereof that follows may be better understood, and in order that the contributions to the art may be appreciated. There are, of course, additional features of the invention that will be described hereinafter and which will also form the subject of the claims appended hereto.

BRIEF DESCRIPTION OF THE DRAWINGS

For detailed understanding, references may made to the detailed description of various disclosed embodiments, taken in conjunction with the accompanying drawings, in which like elements have been given like numerals, wherein.

DESCRIPTION OF EXEMPLARY EMBODIMENTS

Figure 1A:
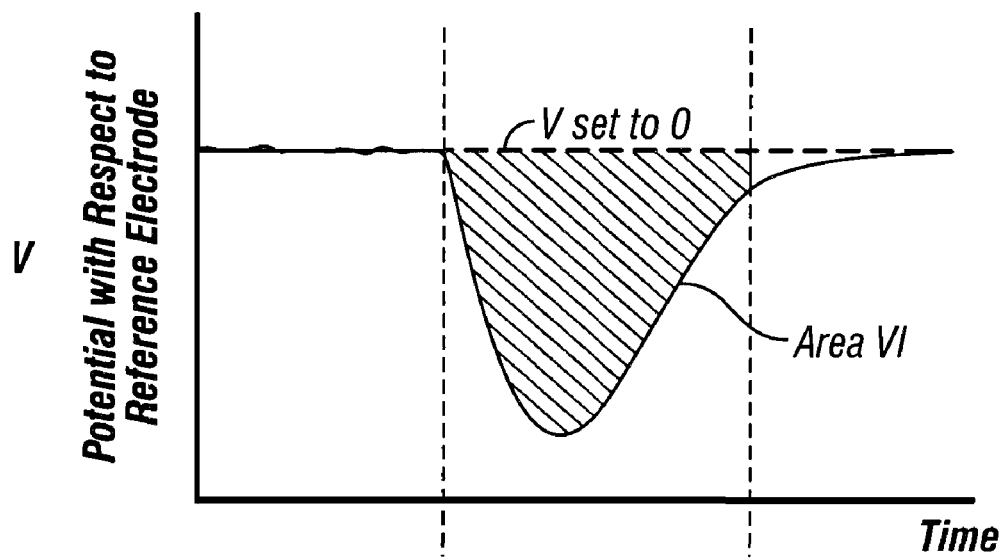
FIG. 1A is a graph of voltage (potential) as a function of time measuring potential of a working electrode.

Methods and apparatus for the detection and characterization of the corrosion behavior in systems where both generalized and localized corrosion occurs (in one non-limiting embodiment, in the form of pitting) and is quantitatively evaluated are described. The severity, frequency and time/space distribution of the generalized and localized events are determined from potential and current measurements recorded from the corroding systems.

More specifically, localized corrosion can be determined semi-quantitatively by measuring the galvanic current between two coupled working electrodes and monitoring the potential of the couple using a third reference electrode. This is typically known as current/voltage (electrochemical) noise (ECN). The technique correlates the two signals using a range of mathematical methods to calculate the general corrosion rate ($R_p = \Delta V/\Delta I$) and estimate the likelihood of localized corrosion ($L \cdot I = \sigma_i/i_{rms}$), where LI refers to Localization Index, $\sigma_i$ refers to the change in current, $i_{rms}$ refers to the root mean square of the current and Rp refers to the Polarization Resistance. The current analysis of localized corrosion based on electrochemical noise provides indications of the likelihood of localized corrosion (LI) without specific reference to the surface affected, or the number and distribution of those localized events. LI relates to the degree of localized corrosion compared to general corrosion, i.e., the greater the LI the higher the probability of localized corrosion.

Another previous method that gives an indication of localized corrosion is by monitoring the potential of a single test electrode with respect to a reference electrode, known as potential noise. This method can detect potential excursions caused by localized events, however without any current information it is not realistically possible in real time to correlate the significance or magnitude of a potential transient in terms of metal loss.

The Localized Corrosion Monitoring (LCM™) technique was developed by switching between periods of potential monitoring and potentiostatic control at the rest potential. During the potentiostatic measurement the polarization of the test electrode is minimized and both current and potential data are obtained. It is possible to identify individual localized events (i.e. transients) through the reconstruction of current transients. This enables a quantitative measurement of the amount of current involved in each event to be obtained, leading to possibilities of measuring the rate of localized corrosion associated with each transient (i.e. pit growth). The LCM technique depends on the analysis of data due to the regular switching between free potential measurement and polarization at the rest potential. Such signals can lead to current transient truncation and thus a possible underestimation of the total charge in each pitting event, i.e. pit depth estimation. This previous LCM technique is contrasted with the present method and apparatus which measures only potential and occasionally makes a LPR polarization.

The present methods and apparatus provide for continuous generalized and localized corrosion monitoring and real time analysis of the monitored data. Real-time system monitoring of the corrosion status of operating equipment is enabled. In laboratory investigations, the invention may provide information simultaneously on generalized and localized corrosion behavior that may be directly correlated with corrosion attacks.

This apparatus and method herein provide continuous monitoring of the sudden changes in the corrosion potential with time and can provide information about generalized and localized corrosion rate and processes. These changes develop dynamically in the form of transient responses in potential transient measurements. While numerous methods have been used to measure general corrosion (e.g. linear polarization resistance (LPR), electrical resistance, EIS, electrochemical noise (ECN)), there have been few analysis methods for characterizing localized corrosion, in particular in conjunction with generalized corrosion.

Figure 1B:
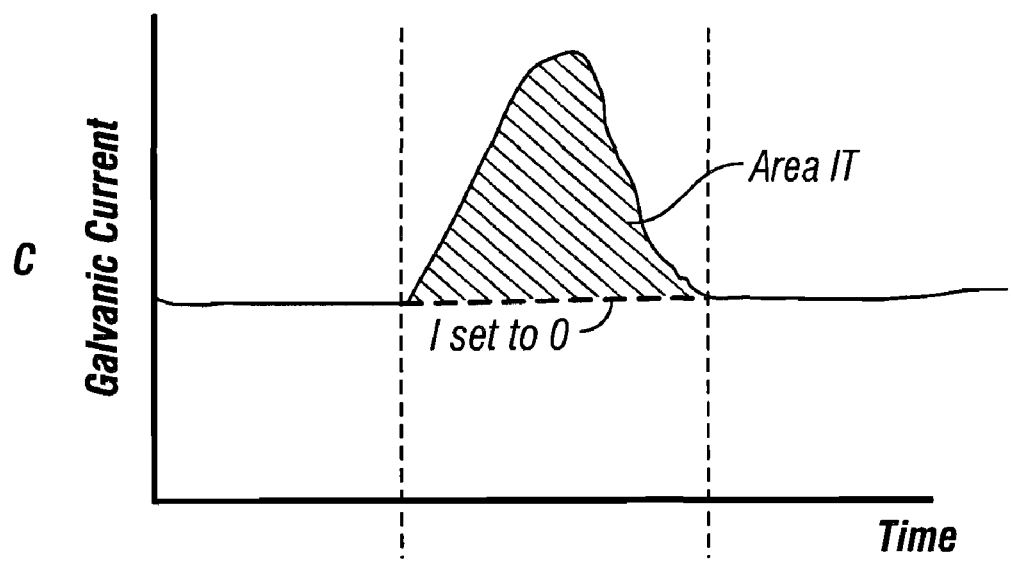
FIG. 1B is a graph of current as a function of the same period of time as FIG. 1A measuring a current transient.

U.S. Pat. No. 6,280,603 to Jovancicevic discloses a potentiostatic electrochemical noise (P-ECN) invention and provides quantitative measure of localized corrosion in terms of type, frequency, distribution and penetration rate. (this patent is hereby fully incorporated herein by reference). Three different types of single current/potential transients may be identified: (i) initiation/propagation (Type I), (ii) initiation/partial repassivation (Type II), (iii) and initiation/repassivation (Type III), and (iv) multiple initiation/propagation (Type IV) transients are recorded over time (FIG. 1 in U.S. Pat. No. '603). The transients may be defined as a sudden cathodic shift in potential or anodic shift in current at open-circuit or constant potential, respectively. For a given system of objects to be monitored, depending on the metal or material examined, a transient may be a potential shift of $\geq 0.5$ mv/sec or an anodic shift of $>0.1$ $\mu A/cm^2/sec$. For some typical systems, the Type I and II transients may be chosen as transients that last, for example, $\leq 5$ seconds, while Type III transients may be chosen as those that last between $\geq 30$ seconds and 200 seconds, and Type IV as those that last $\geq 200$ seconds. The relative differences of the amplitudes and frequencies of various transients may be indicative of the types of corrosive attacks present in any active system. These electrochemical noise data can provide an indication of the type of corrosion damage occurring; and may be used to indicate the nature of localized attack. The severity of localized corrosion may be measured by the penetration rate of individual pits.

Based on the magnitude, duration and relative rate of decrease and/or increase of potential and current signals, four different types of transients can be observed in the LCM time records and classified as: Type I initiation/propagation (IP), Type II initiation/partial repassivation (IPR), Type III initiation/repassivation (IR) and Type IV initiation/repassivation/propagation (IRP) transients. Type III is of less concern because the site of the corrosion undergoes repassivation. Type IV transients are indicative of multiple pits occurring that are generally large in number, more or less active, uniformly distributed, smaller and shallower than the IP (Type I) and IPR (Type II). This transient analysis of the potential/current time dependence may be used in quantifying localized corrosion activity on carbon steel and stainless steel tests.

The occurrence and amplitude of current/potential transients with time are directly related to the number, magnitude (depth) and distribution of localized corrosion events (e.g. pits). Thus, as the transients are longer, and as the amplitudes of the transients are larger the larger the area affected by corrosion. Also when an area affected by corrosion is larger, the depth of the corrosion is less.

By correlating data acquired from monitored systems with the above parameters, information on the severity and the feature of corrosion damage on the monitored objects can be obtained. Similarly, the effectiveness of corrosion control measures, such as chemical inhibition, or the need for such measures, can be determined.

Localized corrosion, as indicated by the previously described transient Types I-IV, means pitting has happened locally and the extent of the event, both area and depth of penetration, may be determined directly from the current and potential measurements.

The methods and apparatus described herein make it easy to convert discrete transients in the potential fluctuations into current data. Individual localized events may be monitored in their entirety and given a meaningful current magnitude. The number of coulombs of current passed by a single transient event can be calculated and related to the magnitude of localized events (e.g. pit depth).

In one non-limiting embodiment, the potential of the working electrodes is monitored with respect to a reference electrode. Periodically, a polarization is applied to the working electrodes around their rest potentials and Rp, determined using LPR, EIS, LCM or ECN, that is related to a typical potential transient caused by a localized corrosion event occurring on the working electrodes, recorded. From the Rp=$\Delta V/\Delta I$ type of relationship, the resultant current response, $\Delta I$ (mirror image of the potential) is calculated and the amount of coulombs passed during the transient recorded. The base line for working out all calculations to do with potential transients is set to the Rest Potential or open circuit potential (OCP) prior to an occurring transient. Potential transients in the unpolarized data can either be detected by examination of the data or by simple automated methods as described previously. Individual data points during the potential transient may also be converted directly to current data points using the same Rp relationship. The magnitude of the coulombs passed by an individual transient is directly related to metal loss caused by a localized corrosion event (see FIG. 7).

Other considerations and features of the methods and apparatus described herein include, but are not necessarily limited to the following.

The reference electrode may be resistant to localized corrosion and hold a steady potential; in a non-limiting example be a saturated calomel electrode.

The system may be used with a two working electrode system, or a three or more electrode system, where the working electrodes are galvanically coupled together.

The polarization is typically applied using a potentiostat, however a galvanostat or other equivalent device could be used in its place and the resultant potential response monitored.

The polarization applied should be representative of the type of transient signal produced by a localized event.

When deciding when to apply the polarization, the rate of change of free potential data should be considered such that the polarization is applied during a less active period.

Optionally, a number of polarizations may be applied to the test electrode in order to get an average response to produce a Rp value for more accurate purposes.

The calibration may be used for data points prior to the polarization. The calibration may be weighted from one calibration ratio to the next in order to give a smooth transition of the calibration.

The application of the polarization should be only a small percentage of the total test time. One guideline is to apply the polarization every hour or at the same rate at which the conditions in the cell are expected to change, if this is more frequent.

More specifically, the technique and system herein uses an optional reference electrode (RE), such as a saturated calomel electrode or other electrode that is resistant to localized corrosion. This may be used to monitor the couple potential of two or more working electrodes (e.g. WE1, WE2) that are coupled to each other as if by wire using low- or Zero-Resistance Ammeters (ZRA) e.g. For simplicity, the couple of either two or more electrodes may be seen as a single electrode. As with LCM, a localized pitting event on one of the electrodes will lead to a potential transient. Also as with LCM the duration of this transient indicates the duration of the pitting event. It is possible to measure the area within the potential transient with the baseline being the initial starting potential. This measurement has units of V⁻ sec.

However, the test electrode is not in fact a single electrode, it comprises two or more galvanically coupled working electrodes.

The invention will now be described with respect to some non-limiting Examples that are simply provided to further illustrate the invention, but not to limit it in any way.

EXAMPLE I

Example I is a simple case where there are just two otherwise identical coupled electrodes. During a localized corrosion event, one of the two electrodes WE1 or WE2 will pit. The pitting process produces a load of electrons. These electrons are quickly distributed between the coupled electrodes WE1 and WE2. The electrons are used up by a cathodic reaction on the two electrodes. It follows that as the coupled electrodes are identical, half the electrons produced by the localized event pass to the non pitting electrode. The ZRA coupling WE1 and WE2 enables one to measure the current flowing between the two electrodes. Thus, half the current due to the pitting event may be monitored. The base line for the current should be taken as the level of current flowing just before the start of the transient. In a two electrode system, it is quite apparent which electrode is pitting due to the direction of the current flow. It is the total number of coulombs that flowed during the period of the transient that is of interest, as this can be directly related to half the metal loss in the localized event. Multiplying the coulombs monitored by two will give the value of the total metal loss caused by the localized event.

In reality the electrode that has the localized event wants to change its potential by a greater amount than the transient produced. In a completely linear system the transient is effectively reduced by half, as another electrode is coupled to the one with the localized corrosion. In effect the non-pitting electrode is polarized by half what would have been the full transient size if the pitting electrode had been left to pit by itself.

It is also possible to monitor the general corrosion rate. We know the level of polarization from the voltage transient, V·T (see FIG. 1A) from the baseline case where V is set to 0; we know the current due to this transient (see FIG. 1B) from the baseline case where I is set to 0. Thus the Polarization Resistance, Rp, may be worked out by a simple method, where Rp=V·T/I·T or V·T/I·T=V/I as the time units cancel out. V·T is termed herein "voulombs" defined as the area under the potential transient and analogous to coulombs (I·T), which is used to calculate metal loss from pitting events. That is, voulombs may be understood as the integration of volts as a function of time. Doing the summation in this way allows for rapid charging and slows discharging of capacitors in the interfacial layers and eliminates the effect of sweep rates affecting the LPR.

Thus, localized corrosion information and general corrosion information are provided in one simple test without any apparent outside polarization.

EXAMPLE II

Figure 2A:
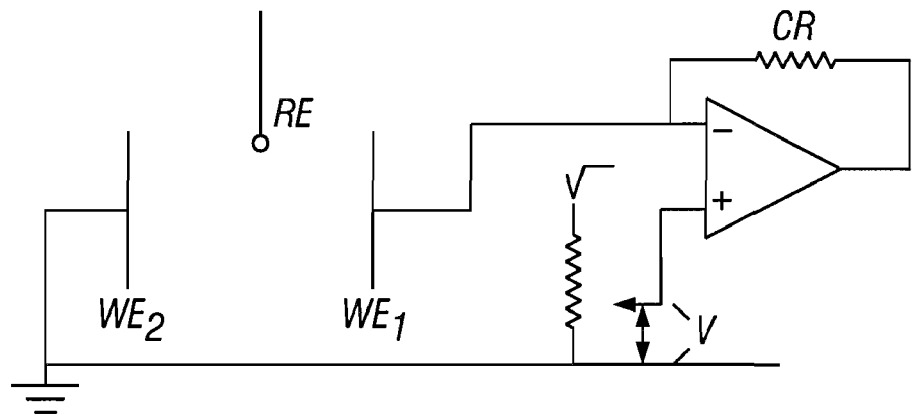
FIG. 2A is a schematic illustration of a system having two non-identical working electrodes and a reference electrode.

There should also be considered a case where the two coupled electrodes are not identical, say brass and aluminum, as shown schematically in FIG. 2A. In this case the numbers of coulombs can not be easily calculated due to the localized event since the cathodic reactions on the two metals are different, so by just measuring the number of coulombs flowing between the two electrodes, it is not readily possible to measure the amount of electrons produced by the localized corrosion site. However it is still possible to measure the general corrosion rate of the electrode without the pit, as the polarization relative to uncoupled electrode and the level of current of the coupled electrode are known.

Figure 2C:
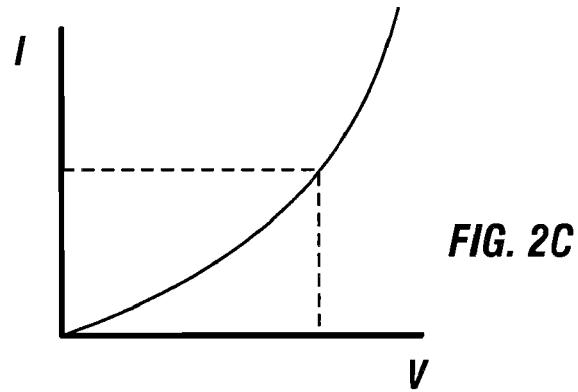
FIG. 2C is a graph of current as a function of voltage for the natural potential transient shown in FIG. 2B and the current transient graphed in FIG. 2D.
Figure 2B:
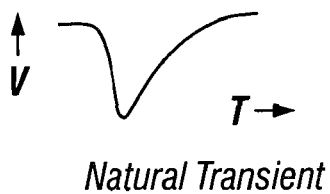
Figure 2D:
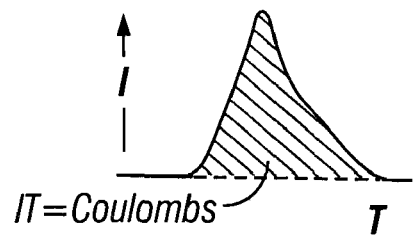

In this case, it will be necessary to apply a polarization to the coupled electrodes in the same way as for standard LCM. Alternatively, one of the coupled working electrodes (WE1 and WE2, where RE refers to the reference electrode) can be offset using a two electrode polarization. That is, polarization is applied by offsetting the ZRA coupling the WEs to calibrate naturally occurring transients and calculate the general corrosion rate of the pitting WE. FIG. 2C is a schematic graph of I as a function of V produced by the calibrating polarization, as it relates to area V·T (voulombs) from FIG. 2B and I·T (coulombs) of FIG. 2D. (Compare FIGS. 2B and 2D to FIGS. 1A and 1B, respectively.)

If the Rp value is known for one of the electrodes, then it is only a bit of calculation to work out the Rp for the other electrode.

$$Rp_t = Rp_1 + Rp_2 \tag{1}$$

where $Rp_t$, $Rp_1$ and $Rp_2$ are total, WE1 and WE2 polarization resistance, respectively. If $Rp_2$ is known then $Rp_1$ may be calculated from $Rp_r$. Once the ratio between $Rp_1$ and $Rp_2$ is known, it is then possible to work out the number of coulombs of current transmitted by the pitting site using the following formula.

For a pit on WE1:

$$Rp_1/Rp_2 = I \cdot T_{tc} / I \cdot T_{ce1} \qquad (2)$$

where $I \cdot T_{tc}$ and $I \cdot T_{ce1}$ are transferred coulombs and consumed coulombs on WE1, respectively.

Rearranging equation (2) in terms of $I \cdot T_{ce1}$, one can obtain:

$$I \cdot T_{ce1} = Rp_2 I \cdot T_{tc} / Rp_1 \qquad (3)$$

The total number of coulombs, $I \cdot T_t$ produced by pit site is thus:

$$I \cdot T_t = I \cdot T_{tc} + I \cdot T_{ce1} = (Rp_1/Rp_2 + 1) \cdot I \cdot T_{tc} \qquad (4)$$

One advantage of this technique is that there is no feedback path for the potentiostat/ZRA through the cell, which is inherently robust.

In a case of working electrodes of dissimilar materials, the standard LCM polarization method can be used. Otherwise one of the working electrodes in the couple, probably the electrode that has previously pitted, can be offset whilst still coupled to the other working electrode(s). The ratio of resistance can then be calculated in a similar way as before, so that it is possible to work out the total number of coulombs transmitted by the pit site.

Figure 3:
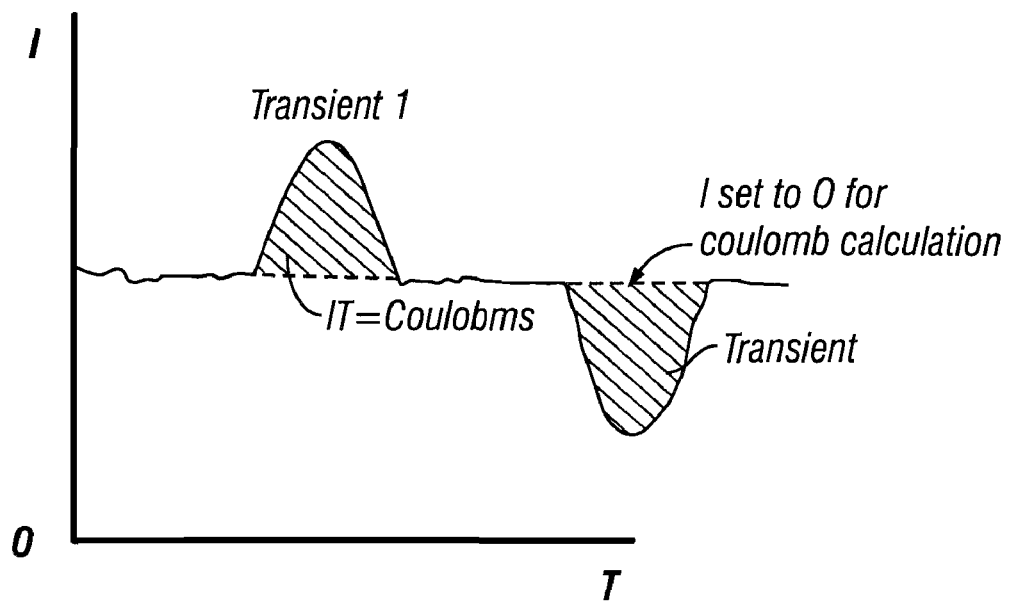
FIG. 3 is a graph of current as a function of time for two galvanically coupled working electrodes with no reference electrode present during two transients.

In the case of a coupled two electrode system, it is not necessary to have a reference electrode. A galvanic couple will suffice for two near identical electrodes. In this case one simply needs to look for the transient in the current information. Please see FIG. 3 for two galvanically coupled electrodes with no RE, where as in FIG. 2, V=0 (no potential difference between electrodes) and where $I \cdot T_{tc}$ is essentially equal to $I \cdot T_{ce1}$; Transients 1 and 2, respectively. As one does not have potential information, a general corrosion rate cannot be produced without offsetting one of the electrodes. This is, however, of a particular interest as it provides information on localized corrosion while being very robust when it comes to a two electrode system.

It is expected that in most, if not all, situations in the field the electrodes will not be identical, thus a reference electrode would be very helpful. Also, in general even though the electrodes may not be identical in size, it is very helpful for them to be made of the same material. As such, they may have very different sizes as noted below in Example IV. In non-limiting examples, the ratio of the areas of the electrodes may be 2/1 or 5/2, although this complicates the mathematics unless the ratio is very small/very large. In another non-limiting embodiment the ratio of the areas may be greater than 10 to 1.

EXAMPLE III

The next case to consider is multiple working electrode couples. For instance, in the case of a segmented weld with five electrodes coupled via ZRAs, the same theories and principles hold up as well. If all the elements are pretty much identical, then a single pit site can give the LPR value and total number of coulombs passed by the pit site. In this case with identical electrodes, the number of coulombs passed to the other electrodes via the ZRAs is 5/4×the transfer current.

EXAMPLE IV

Figure 4A:
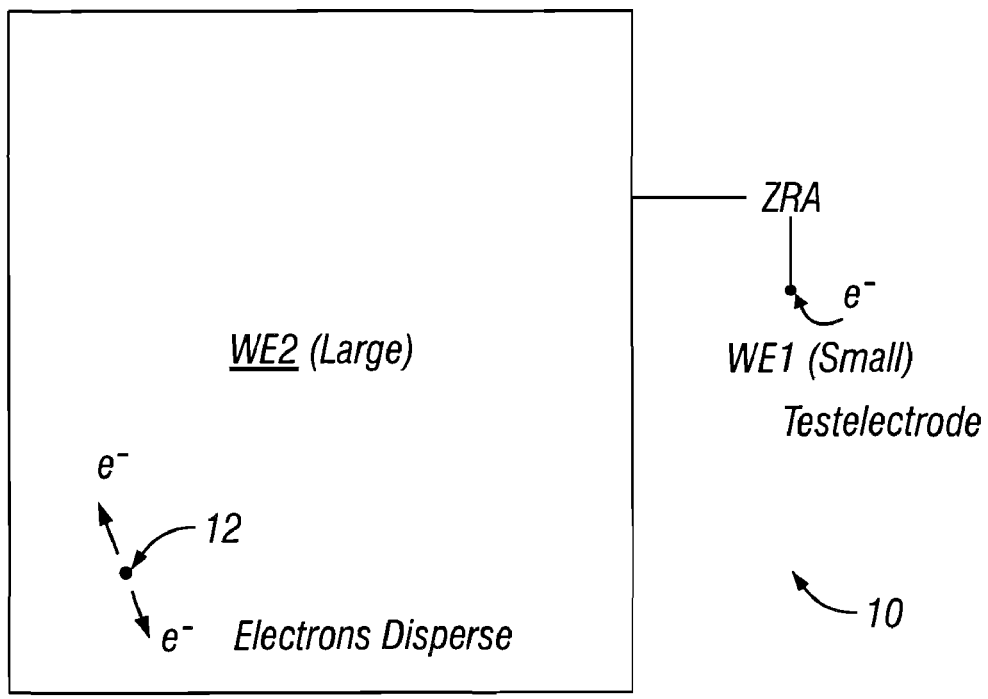
FIG. 4A is a schematic illustration of a two working electrodes coupled by a ZRA, where WE1 is representative of a relatively small probe and WE2 is representative of a relatively much larger object such as a pipeline or downhole pipe.
Figure 4B:
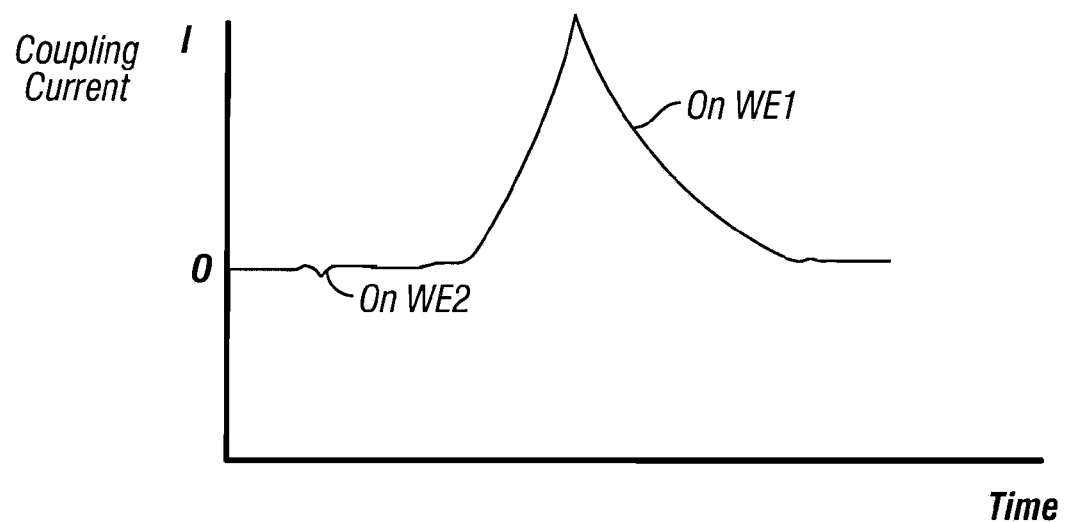
FIG. 4B is a graph of current as a function of time for the system illustrated in FIG. 4A.

For on site or field work, either down hole or in a pipe, it is only necessary to have a single WE1 (a probe) coupled to the rest of the pipe or other relatively large metal object (WE2) as schematically illustrated for system 10 in FIG. 4A. Here, WE2 is significantly larger than WE1, in one non-limiting instance at least 10 times larger. During pitting, electrons $e^-$ disperse rapidly from pitting site 12 and rush to WE2 for dispersal and consumption. However, only a small fraction of those electrons transfer over to the test electrode WE2. This is shown graphically in FIG. 4B as a small transient labeled "On WE2". The share of electrons going over to WE2 is heavily related to the fraction: Surface Area of WE1/Surface Area of WE2. In this case near 0% of the transient current is monitored by the ZRA. Any localized event occurring on the pipe WE2 will be of no importance. Consider now a nearly similar pitting event occurring on the small electrode WE1 with an equivalent amount of metal loss as for the previously discussed pitting event on WE2. Referring to FIG. 4B, the pitting event produces the transient labeled "On WE1". In this case the electrons produced by the pitting event on electrode WE1 only have a small surface area to be consumed by a cathodic reaction, so nearly all of them rush over to the large electrode WE2 for ease of consumption in a cathodic reaction. Due to the vast difference in areas of the electrodes, a value close to 100% of the electrons produced by a pitting event on WE1 is monitored as current flow between WE1 and WE2.

During a pitting event on WE1, the vast majority of electrons produced rush to WE2. During a pitting event on WE2, only a minority of electrons produced go to WE1.

EXAMPLE V

Figure 5:
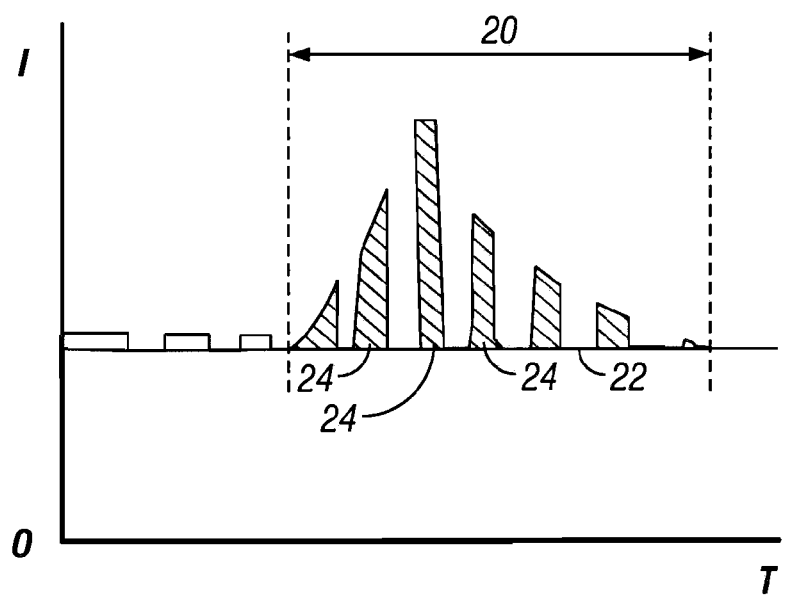
FIG. 5 is a graph of current as a function of time for a multiphase flow system marking a transient represented as a series of peaks.

The methods herein may be taken further to the case of transient detection in multiphase flow monitoring. Multiphase flow or a multiphase fluid are defined herein as a mixture of an aqueous phase (e.g. water) with a non-aqueous phase (e.g. hydrocarbon). In this case a two working electrode system is contemplated without a reference electrode. Transients in the current data can be detected in the normal way. They will appear differently however, as schematically illustrated in FIG. 5. It is expected that the overall curve will still have the current transient shape, but it may appear as vertical bands, analogous to a bar code. The current baseline is represented at 22, where the transient is detected over time 20, and the area of the peaks 24 are added to calculate the coulombs due to the transient.

Assuming distinct periods of conductivity followed by non-conductivity, then in this case the coulombs due to the pitting event will still be twice the number of coulombs monitored. General corrosion rates can be measured using the ACM Instruments method of GB 2365977 A for monitoring in multiphase environments. It is very robust as it does not use a reference electrode. A two electrode probe is particularly suitable for this type of applications. Alternatively, a single electrode probe with the pipe as the other electrode can be used as in Example IV.

The methods and apparatus described herein allow for determinations of changes in the rate of propagation of the depth of pits with time, or penetration rate, from the measured transients of any one of Types I-IV. Using this information the approximate mass or volume of metal corroded due to localized corrosion can be determined. The present invention therefore allows for accurate determination the number of pits that occur and their depth of penetration. The assumption that all or almost all of the corrosion is localized corrosion is strengthened by the fact that the types of corrosion described herein above, especially the "active" Type I and II transients, directly indicate ongoing localized corrosion. Without the transients that indicate localized corrosion there would be no analysis of corrosion penetration rates.

As previously mentioned, prior art techniques have measured potential and current by alternating measurements of regular periods, for example 30 seconds each. To obtain the most accurate measurements with the present methods and apparatus, it is desirable to acquire measurements of the current transient throughout the time period that a pitting event occurs, and therefore the measurement of current may last considerably longer than 30 seconds. Transient event monitoring software allowing this monitoring that recognizes types of transients during their occurrence may be provided as part of methods and apparatus herein.

The present methods and apparatus provide for features including, but not necessarily limited to, an internal potentiostat, a low-resistance or zero-resistance ammeter and internal PC (personal computer) or other computing apparatus for monitoring, measuring and analyzing data. The PC may include any operating system and run software for data analysis that accomplishes the purposes and goals described herein.

In another embodiment, the methods and apparatus are implemented as a set computer-executable of instructions on a computer readable medium, comprising ROM, RAM, CD-ROM, Flash RAM or any other computer readable medium, now known or unknown that when executed cause a computer to implement the functions of the present invention.

The present apparatus and methods relate to measuring corrosion parameters on a metallic surface using a unique electrochemical technique.

For ease of analysis, the reference electrode should not be made of the same material as the test electrode. It should be made of a material that is much more resistant to localized corrosion than the test electrode. If it is made of the same material, then the reference electrode will also be subject to the same localized corrosion as the test or working electrode. During a pitting event on the test or working electrode, the reduction in potential helps to inhibit pits occurring elsewhere on that electrode. However, there is no such mechanism between the reference and the working electrode. It would for instance be possible to have a very large transient occurring at the same time, one on the working electrode and the other on the reference electrode. The resultant potential monitored would indicate that nothing had happened if the transients were identical. The reference electrode may be of a material including, but not necessarily limited to, saturated calomel, platinum, nickel-based (e.g., Hastalloy C276), iron based (e.g., stainless steel) or a chromium-based alloy, or mixtures and alloys thereof, or any other electrically conductive, non-corrosive material.

In operation, the test or working and reference electrodes are disposed in the same or very similar environment as the component of interest, in a spaced relation to one another. Typically the environment is a corrosive liquid medium, particularly an acidic liquid medium. This technique primarily monitors the potential of a galvanic couple with respect to time. Transients caused by a localized event may be detected in the potential data which give the duration and potential magnitude associated with the localized event. During the localized event the change in the magnitude of the current may be monitored. The areas underneath the potential and current transients have units of Volts-Time (coulombs) and Current-Time (coulombs), respectively. The division of voulombs by coulombs cancels out time to give a value of Rp or polarization resistance for the electrodes. The area to use in a simple case with identical electrodes is the area of one of the electrodes. The quantity of coulombs measured is, in a simple case with coupled electrodes of similar material and surface area, doubled to work out the metal loss by the site undergoing localized corrosion. There will be some errors in this approach due to solution resistance, however if conductivity is reasonable, then this error will be minimal. Please see the discussion with respect to Example I.

If no reference electrode is used, then transients may be detected in the current data obtained between two galvanically coupled electrodes. The quantity of charge associated with the localized event may be calculated as double the area within the transient on a Current v Time graph. It is not possible to calculate the general corrosion rate using this method alone as no potential information is available. However, an occasional polarization between the two electrodes will give the general corrosion rate in the normal way.

While various embodiments and alternatives have been shown and described, various modifications and substitutions may be made thereto without departing from the spirit and scope of the invention, which are defined only by the appended claims. Accordingly, it is to be understood that the present invention has been described by way of illustrations and not limitation. For instance, alternative devices and machines may be employed to collect and analyze the data other than those specifically mentioned. There are some variations to these methods and apparatus as previously discussed that allow for the use of multiple electrode couples, dissimilar electrodes, electrodes of different area and use in multiphase environments. However, these variations generally involve adapting simple mathematics and a variation on the above themes.

What is claimed is:

1. A method for measuring generalized corrosion and localized corrosion rates comprising:
   (a) placing at least three electrodes in proximity to one another, where
      i. at least two working electrodes are galvanically coupled via a zero- or low-resistance ammeter used to monitor the potential of the electrodes, and
      ii. a reference electrode of a material resistant to localized attack used to monitor the potential of the galvanically coupled electrodes;
   (b) detecting transients in potential data for a localized corrosion event and calculating an area within the transient having units of volts-time;
   (c) calculating the change in the magnitude of the current data passed during the potential transient for the same time period as (b) and giving it a value with units of current-time (coulombs);
   (d) dividing the volts-time by the current-time to give the polarization resistance (Rp) as a measure of general corrosion rate; and
   (e) doubling the charge in (c) to calculate the metal loss caused by the localized corrosion event.

2. The method of claim 1 where in (a) only two galvanically coupled working electrodes are placed, where the method further comprises applying an occasional polarization to the working electrodes to determine the general corrosion rate by offsetting one of the electrodes against the other.

3. The method of claim 1 where in (a) the surface area of one of the two galvanically coupled working electrodes is at least 2 times larger than the other, where the method further comprises monitoring the number of coulombs as a direct measurement of metal loss of a localized corrosion event on the smaller working electrode, where the electron consumption is split in the same ratio as the surface area of the electrodes.

4. The method of claim 1 further comprises placing more than two galvanically coupled electrodes.

5. The method of claim 1 further comprising placing the electrodes in a multiphase fluid.

6. The method of claim 1 where the galvanically coupled electrodes are of dissimilar materials, further comprising calculating the corrosion activity on an electrode experiencing a localized corrosion event from the potential transient and current transient, and further applying a polarization to the working electrodes and calculating the level of metal loss if the localized corrosion event and the level of general corrosion activity on the electrode experiencing a localized corrosion.

7. The method of claim 1 where the electrodes are placed in a solution, and where the method further comprises using an AC signal to calibrate for solution resistance.

8. A method for measuring generalized corrosion and localized corrosion rates comprising:
   (a) placing at least three electrodes in proximity to one another in a corrosive acid solution, where
      i. at least two working electrodes are galvanically coupled via a zero- or low-resistance ammeter used to monitor the potential of the electrodes, and
      ii. a reference electrode of a material resistant to localized attack used to monitor the potential of the galvanically coupled electrodes;
   (b) detecting transients in potential data for a localized corrosion event and calculating an area within the transient having units of volts-time;
   (c) calculating the change in the magnitude of the current data passed during the potential transient for the same time period as (b) and giving it a value with units of current-time (coulombs);
   (d) dividing the volts-time by the current-time to give the polarization resistance (Rp) as a measure of general corrosion rate; and
   (e) doubling the charge in (c) to calculate the metal loss caused by the localized corrosion event.

9. The method of claim 8 where in (a) only two galvanically coupled working electrodes are placed, where the method further comprises applying an occasional polarization to the working electrodes to determine the general corrosion rate by offsetting one of the electrodes against the other.

10. The method of claim 8 where in (a) the surface area of one of the two galvanically coupled working electrodes is at least 2 times larger than the other, where the method further comprises monitoring the number of coulombs as a direct measurement of metal loss of a localized corrosion event on the smaller working electrode, where the electron consumption is split in the same ratio as the surface area of the electrodes.

11. The method of claim 8 further comprises placing more than two galvanically coupled electrodes.

12. The method of claim 8 where the corrosive acid solution is a multiphase fluid.

13. The method of claim 8 where the galvanically coupled electrodes are of dissimilar materials, further comprising calculating the corrosion activity on an electrode experiencing a localized corrosion event from the potential transient and current transient, and further applying a polarization to the working electrodes and calculating the level of metal loss if the localized corrosion event and the level of general corrosion activity on the electrode experiencing a localized corrosion.

* * * * *